(12) United States Patent
Wise et al.

(10) Patent No.: US 7,018,356 B2
(45) Date of Patent: Mar. 28, 2006

(54) METHOD AND APPARATUS FOR ADJUSTING THE CONTENTS OF A NEEDLE-LESS INJECTOR

(76) Inventors: Roger R. Wise, 10700 Farralone Ave., Chatsworth, CA (US) 91311; Seth D. Levy, 612 N. Formosa Ave., Los Angeles, CA (US) 90036

( * ) Notice: Subject to any disclaimer, the term of this patent is extended or adjusted under 35 U.S.C. 154(b) by 370 days.

(21) Appl. No.: 10/285,687

(22) Filed: Oct. 31, 2002

(65) Prior Publication Data

US 2004/0087896 A1 May 6, 2004

(51) Int. Cl.
*A61M 5/30* (2006.01)
*A61M 37/00* (2006.01)

(52) U.S. Cl. .................................. 604/68; 604/131

(58) Field of Classification Search ............ 604/46, 604/68, 69, 70, 93.01, 131, 134, 135, 140, 604/141, 143, 145, 146, 181, 187, 207, 208, 604/218, 228

See application file for complete search history.

(56) References Cited

U.S. PATENT DOCUMENTS

| | | |
|---|---|---|
| 1,997,129 A | 4/1935 | Taylor et al. |
| 2,221,739 A | 11/1940 | Reiter |
| 2,605,763 A | 8/1952 | Smoot |
| 2,632,445 A | 3/1953 | Kas, Sr. |
| 2,642,062 A | 6/1953 | May |
| 2,680,439 A | 6/1954 | Sutermeister |
| 2,695,023 A | 11/1954 | Brown |
| 2,718,299 A | 9/1955 | Atwater et al. |
| 2,754,818 A | 7/1956 | Scherer |
| 3,110,310 A | 11/1963 | Cislak |
| 3,131,692 A | 5/1964 | Love |
| 3,141,583 A | 7/1964 | Mapel et al. |
| 3,293,749 A | 12/1966 | George et al. |
| 3,348,545 A | 10/1967 | Sarnoff et al. |
| 3,481,510 A | 12/1969 | Allen |
| 3,507,276 A | 4/1970 | Burgess |
| 3,517,668 A | 6/1970 | Brickson |
| 3,557,784 A | 1/1971 | Shields |
| 3,568,736 A | 3/1971 | Linch et al. |
| 3,583,399 A | 6/1971 | Ritsky |
| 3,688,765 A | 9/1972 | Gasaway |
| 3,695,266 A | 10/1972 | Lussier |
| 3,853,125 A | 12/1974 | Clark et al. |
| 3,859,996 A | 1/1975 | Mizzy et al. |
| 3,894,663 A | 7/1975 | Carhart et al. |

(Continued)

FOREIGN PATENT DOCUMENTS

| | | |
|---|---|---|
| CA | 1103314 | 2/1978 |
| CA | 1258 019 | 8/1989 |
| CH | 293302 | 8/1951 |
| DE | 22140 | 7/1882 |
| DE | 730971 | 1/1943 |
| DE | 1170436 | 11/1962 |
| DE | 1070 784 | 5/1964 |
| EP | 0037 696 | 3/1981 |
| EP | 0143 895 | 8/1984 |

(Continued)

*Primary Examiner*—Nicholas D. Luchesi
*Assistant Examiner*—Mark K. Han
(74) *Attorney, Agent, or Firm*—Pillsbury Winthrop LLP

(57) ABSTRACT

A method and apparatus for adjusting the contents of a needle-less injector that contains an injectable product are described. A needle-less injector includes an adjustment switch in mechanical contact with the driver of a needle-less injector. A user may displace the adjustment switch to expel air or gas contained in the product section of the needle-less injector prior to administration of a needle-less injection with the same. The adjustment switch may alternatively or additionally be used to expel at least a portion of the injectable product contained in the needle-less injector to reduce the volume of the product to be injected with the needle-less injector.

28 Claims, 16 Drawing Sheets

U.S. PATENT DOCUMENTS

| | | |
|---|---|---|
| 3,946,732 A | 3/1976 | Hurscham |
| 3,977,574 A | 8/1976 | Thomas |
| 4,022,207 A | 5/1977 | Citrin |
| 4,031,892 A | 6/1977 | Hurschman |
| 4,033,378 A | 7/1977 | Pauliukonis |
| 4,099,548 A | 7/1978 | Sturm et al. |
| 4,114,619 A | 9/1978 | Wagner |
| 4,139,008 A | 2/1979 | Wagner |
| 4,146,029 A | 3/1979 | Ellinwood, Jr. |
| 4,169,474 A | 10/1979 | Wagner |
| 4,284,077 A | 8/1981 | Wagner |
| 4,333,458 A | 6/1982 | Margulies et al. |
| 4,338,980 A | 7/1982 | Schwebel et al. |
| 4,393,870 A | 7/1983 | Wagner |
| 4,395,921 A | 8/1983 | Oppenlander |
| 4,413,760 A | 11/1983 | Paton |
| 4,415,101 A | 11/1983 | Shapiro et al. |
| 4,425,121 A | 1/1984 | Young et al. |
| 4,444,560 A | 4/1984 | Jacklich |
| 4,457,712 A | 7/1984 | Dragan |
| 4,470,317 A | 9/1984 | Sabloewski et al. |
| 4,475,905 A | 10/1984 | Himmelstrup |
| 4,498,904 A | 2/1985 | Turner et al. |
| 4,526,294 A | 7/1985 | Hirschmann et al. |
| 4,529,401 A | 7/1985 | Leslie et al. |
| 4,573,970 A | 3/1986 | Wagner |
| 4,581,022 A | 4/1986 | Leonard et al. |
| 4,592,745 A | 6/1986 | Rex et al. |
| 4,596,556 A | 6/1986 | Morrow et al. |
| 4,600,403 A | 7/1986 | Wagner |
| 4,613,328 A | 9/1986 | Boyd |
| 4,659,327 A | 4/1987 | Bennett et al. |
| 4,664,128 A | 5/1987 | Lee |
| 4,676,781 A | 6/1987 | Phillips et al. |
| 4,680,027 A | 7/1987 | Parsons et al. |
| 4,710,172 A | 12/1987 | Jacklich et al. |
| 4,710,178 A | 12/1987 | Leonard et al. |
| 4,722,728 A | 2/1988 | Dixon |
| 4,743,229 A | 5/1988 | Chu |
| 4,790,824 A | 12/1988 | Morrow et al. |
| 4,820,287 A | 4/1989 | Leonard |
| 4,834,149 A | 5/1989 | Fournier et al. |
| 4,865,591 A | 9/1989 | Sams |
| 4,874,367 A | 10/1989 | Edwards |
| 4,883,472 A | 11/1989 | Michel |
| 4,913,699 A | 4/1990 | Parsons |
| 4,936,833 A | 6/1990 | Sams |
| 4,941,880 A | 7/1990 | Burns |
| 4,950,246 A | 8/1990 | Muller |
| 4,959,056 A | 9/1990 | Dombrowski et al. |
| 4,998,570 A | 3/1991 | Strong |
| 5,009,634 A | 4/1991 | Feldman et al. |
| 5,009,637 A | 4/1991 | Newman et al. |
| 5,024,656 A | 6/1991 | Gasaway et al. |
| 5,064,413 A | 11/1991 | McKinnon et al. |
| 5,085,642 A | 2/1992 | Sarnoff et al. |
| 5,088,996 A | 2/1992 | Kopfer et al. |
| 5,092,842 A | 3/1992 | Bechtold et al. |
| 5,102,393 A | 4/1992 | Sarnoff et al. |
| 5,104,380 A | 4/1992 | Holman et al. |
| 5,112,317 A | 5/1992 | Michel |
| 5,114,406 A | 5/1992 | Gabriel et al. |
| 5,139,484 A | 8/1992 | Hazon et al. |
| 5,180,371 A | 1/1993 | Spinello |
| 5,226,895 A | 7/1993 | Harris |
| 5,226,896 A | 7/1993 | Harris |
| 5,244,461 A | 9/1993 | Derlien |
| 5,244,465 A | 9/1993 | Michel |
| 5,249,584 A | 10/1993 | Karkar et al. |
| 5,254,100 A | 10/1993 | Huband |
| 5,267,977 A | 12/1993 | Feeney, Jr. |
| 5,279,584 A | 1/1994 | Dillard, III et al. |
| 5,279,585 A | 1/1994 | Balkwill |
| 5,279,586 A | 1/1994 | Balkwill |
| 5,330,430 A | 7/1994 | Sullivan |
| 5,342,309 A | 8/1994 | Hausser |
| 5,354,287 A | 10/1994 | Wacks |
| 5,383,865 A | 1/1995 | Michel |
| 5,425,716 A | 6/1995 | Kawasaki et al. |
| 5,429,602 A | 7/1995 | Hauser |
| 5,445,620 A | 8/1995 | Haber et al. |
| 5,480,381 A | 1/1996 | Weston |
| 5,499,972 A | 3/1996 | Parsons |
| 5,503,627 A | 4/1996 | McKinnon et al. |
| 5,509,905 A | 4/1996 | Michel |
| 5,520,639 A | 5/1996 | Peterson et al. |
| 5,536,249 A | 7/1996 | Castellano et al. |
| 5,540,664 A | 7/1996 | Wyrick |
| 5,569,189 A | 10/1996 | Parsons |
| 5,593,388 A | 1/1997 | Phillips |
| 5,593,390 A | 1/1997 | Castellano et al. |
| 5,630,796 A | 5/1997 | Bellhouse et al. |
| 5,649,912 A | 7/1997 | Peterson |
| 5,704,911 A | 1/1998 | Parsons |
| 5,713,873 A | 2/1998 | Jehle |
| 5,728,074 A | 3/1998 | Castellano et al. |
| 5,730,723 A | 3/1998 | Castellano et al. |
| 5,746,714 A | 5/1998 | Salo et al. |
| 5,820,602 A | 10/1998 | Kovelman et al. |
| 5,851,198 A | 12/1998 | Castellano et al. |
| 5,891,085 A | 4/1999 | Lilley et al. |
| 5,891,086 A | 4/1999 | Weston |
| 5,891,092 A | 4/1999 | Castellano |
| 5,893,397 A | 4/1999 | Peterson et al. |
| 5,899,880 A | 5/1999 | Bellhouse et al. |
| 5,925,021 A | 7/1999 | Castellano et al. |
| 5,957,166 A | 9/1999 | Safabash |
| 5,957,886 A | 9/1999 | Weston |
| 5,993,412 A | 11/1999 | Deily et al. |
| 6,063,053 A | 5/2000 | Castellano et al. |
| 6,080,130 A | 6/2000 | Castellano |
| 6,096,002 A | 8/2000 | Landau |
| 6,132,395 A | 10/2000 | Landau et al. |
| 6,135,979 A | 10/2000 | Weston |
| D434,323 S | 11/2000 | Pattison |
| 6,145,762 A | 11/2000 | Orloff et al. |
| 6,149,625 A | 11/2000 | Weston et al. |
| 6,156,008 A | 12/2000 | Castellano |
| 6,168,587 B1 | 1/2001 | Bellhouse et al. |
| 6,174,304 B1 | 1/2001 | Weston |
| 6,210,359 B1 | 4/2001 | Patel et al. |
| 6,223,786 B1 | 5/2001 | Castellano |
| 6,264,629 B1 | 7/2001 | Landau |
| 6,302,160 B1 | 10/2001 | Castellano |
| 6,309,371 B1 | 10/2001 | Deboer et al. |
| 6,319,224 B1 | 11/2001 | Stout et al. |
| 6,383,168 B1 | 5/2002 | Landau et al. |
| 6,406,455 B1 | 6/2002 | Willis et al. |
| 6,425,879 B1 | 7/2002 | Egger et al. |
| 6,620,135 B1 * | 9/2003 | Weston et al. .............. 604/140 |
| 2001/0039394 A1 | 11/2001 | Weston |
| 2002/0099329 A1 | 7/2002 | Castellano |

FOREIGN PATENT DOCUMENTS

| | | |
|---|---|---|
| EP | 0220 146 | 10/1986 |
| EP | 0295 917 | 6/1988 |
| EP | 0327 910 | 1/1989 |
| EP | 0347 190 | 6/1989 |
| EP | 0368 191 | 11/1989 |
| EP | 0416 975 | 8/1990 |
| EP | 0427 457 | 11/1990 |

| | | | | | |
|---|---|---|---|---|---|
| FR | 1149 735 | 6/1963 | WO | 92/13583 | 2/1992 |
| FR | 1378829 | 11/1964 | WO | 93/10838 | 11/1992 |
| FR | 1170 312 | 4/1965 | WO | 95/03844 | 7/1994 |
| FR | 1099488 | 10/1965 | WO | 9529720 | 11/1995 |
| FR | 1445 659 | 4/1966 | WO | 96/19252 | 12/1995 |
| FR | 2557 445 | 12/1984 | WO | 96/28202 | of 1996 |
| FR | 2 749169 | 6/1996 | WO | 97/13537 | 10/1996 |
| GB | 1225 495 | 6/1967 | WO | 97/25015 | 1/1997 |
| GB | 1574 267 | 2/1978 | WO | 00/48654 | 8/2000 |
| GB | 2109 690 | 2/1982 | WO | 64514 | 11/2000 |
| WO | 85/02546 | 10/1984 | | | |
| WO | 89/08469 | 3/1989 | | | |

\* cited by examiner

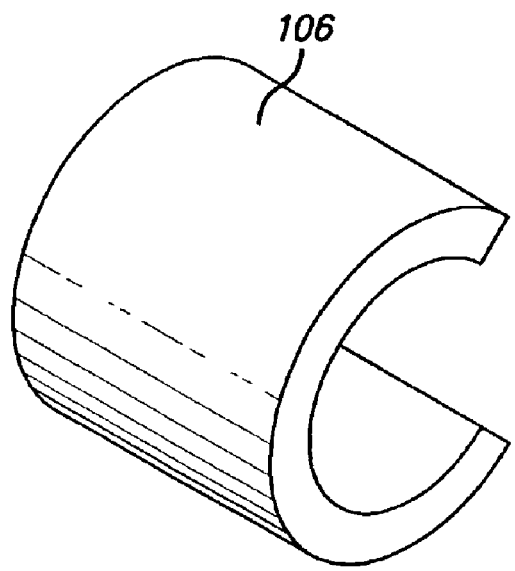
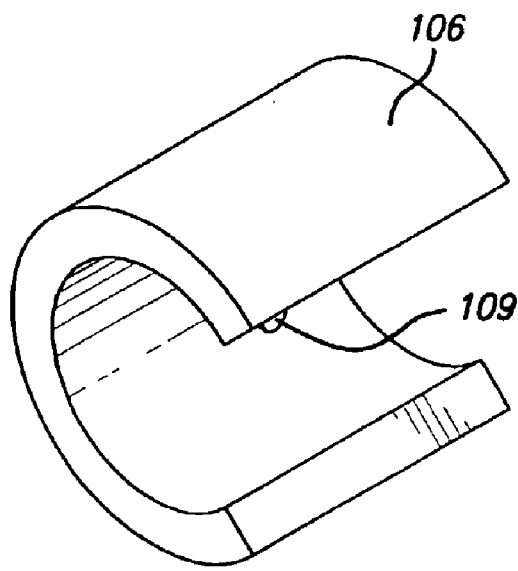
FIG. 4a
FIG. 4b
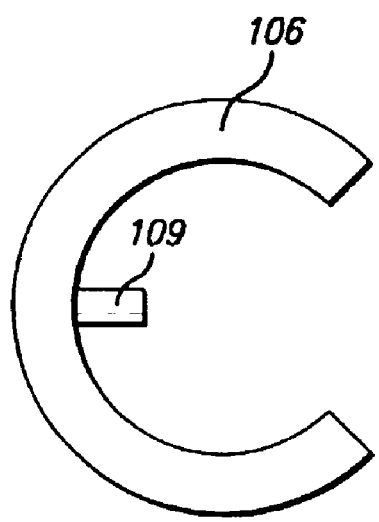
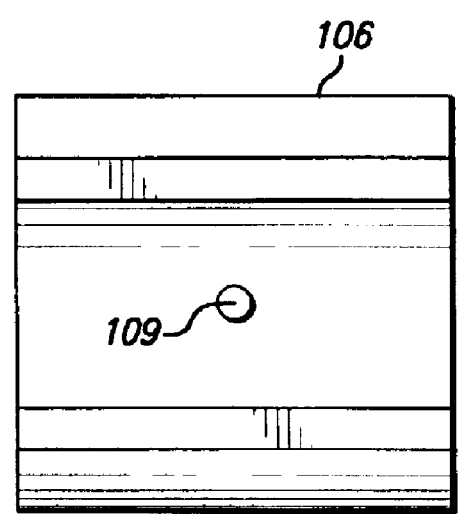
FIG. 4c
FIG. 4d

METHOD AND APPARATUS FOR ADJUSTING THE CONTENTS OF A NEEDLE-LESS INJECTOR

FIELD OF THE INVENTION

This invention relates to needle-less injectors, and in particular, to methods and devices for adjusting the contents of a needle-less injector once the same is filled with an injectable product, prior to the administration of an injection.

BACKGROUND OF THE INVENTION

Traditionally, fluids such as medications are injected into patients, either subdermally or intradermally, using hypodermic syringe needles. The body of the syringe is filled with the injectable fluid and, once the needle has pierced the patient's skin, the syringe plunger is depressed so as to expel the injectable fluid out of an opening in the needle. The person performing the injection is usually a trained medical services provider, who manually inserts the hypodermic needle between the layers of a patient's skin for an intradermal injection, or beneath the skin layers for a subcutaneous injection.

Intradermal or subdermal delivery of a medication through the use of a hypodermic needle requires some skill and training for proper and safe administration. In addition, the traditional method of intradermal injections requires actual physical contact and penetration of a needle through the skin surface of the patient, which can be painful for the patient. Traditional needle injectors, such as hypodermic syringes, are also expensive to produce and difficult to use with prepackaged medication doses. Needle injectors also suffer from increased danger of contamination exposure to health care workers administering the injections, and to the general public when such injectors are not properly disposed of.

Needle-less injectors are designed to obviate some or all of the aforementioned limitations associated with hypodermic needle syringes; although in overcoming such limitations, needle-less injectors present difficulties of their own. One such difficulty is the removal of air or gas from that portion of a needle-less injector that contains the injectable product (e.g., a pharmaceutical solution), especially when the amount of air or gas contained in that portion is or becomes substantial. At least three mechanisms may give rise to air or gas in that portion of a needle-less injector that contains the injectable product: (1) the physiochemical separation of dissolved gas from the injectable product (e.g., during storage of a needle-less injector pre-filled with an injectable product), (2) the introduction of air into the needle-less injector by turbulent filling conditions (e.g., during introduction of an injectable product into the needle-less injector), and (3) loading a needle-less injector with an insufficient quantity of the injectable product to adequately fill the injector.

Regardless of the mechanism responsible for the presence of air or gas in a needle-less injector, subdermal hematomas, tissue damage, and scarring from mechanical force injury may result when pockets of such air or gas are present in an injector prior to dispensing the injectable product contained therein. Within the optimal range for acceleration of liquid medication through the skin via a needle-less injector, liquid readily penetrates the skin while air or gas does not. Thus, air or gas pockets accelerated against the skin lead to the formation of a bruise and can be quite painful for the recipient, whereas liquid medication passes into and/or through the skin without discomfort.

Furthermore, when a cap is removed from the end of a pre-filled needle-less injector, exposing the dispensing area for application to the skin surface, any air or gas pocket not already situated at the dispensing end may tend to migrate toward that end, due to the pressure change caused by cap removal. This motion of the air or gas pocket may force some of the injectable product from the needle-less injector, thereby diminishing the volume of the product that will be injected into the recipient. This may render the dosage level inaccurate, if a nontrivial volume of the product is lost from the injector prior to use.

In the context of injection by more traditional means such as with a preloaded syringe, it is well established that any significant amount of air or gas in such a device will cause pain for the recipient and potentially far more dire consequences if the amount of air is substantial. Air or gas pockets may develop in these syringes much in the way described above with regard to needle-less injectors, as these devices are frequently subject to similar filling and storage conditions. However, those administering traditional injections can readily obviate these limitations by evacuating air from the liquid-containing chamber of a syringe by partially depressing the plunger while the syringe is inverted immediately prior to administration of an injection. This is generally not possible with conventional needle-less injectors, as the entire volume of a needle-less injector ampoule is generally evacuated in one step during normal operation.

Notwithstanding the possible development of an air or gas bubble therein, conventional, pre-filled needle-less injectors generally contain a fixed amount of an injectable product, and the entire fixed amount of this injectable product is injected upon actuation of the needle-less injector. For instance, if a conventional needle-less injector contains a 0.5 ml dosage of a pharmaceutical product, then the entire 0.5 ml volume is generally administered to a recipient of the injection upon a one-time actuation of the needle-less injector. This fixed attribute of conventional needle-less injectors presents difficulty to those for whom the volume of a pre-filled needle-less injector does not correlate with their physiological or therapeutic needs.

This problem generally manifests in one of two types of injection recipient, although the need to adjust the volume of a needle-less injection is by no means limited to these scenarios: (1) injection recipients for whom the pre-filled volume of a needle-less injection is too large, and (2) injection recipients for whom the volume of required injections varies over a period of time. For example, a 0.5 ml volume of a pharmaceutical product may be suitable for the treatment of a disease condition in an average adult, yet a child may require a significantly smaller dosage. Alternatively, particular disease conditions may be treated with periodic injections of a pharmaceutical product, yet the required bolus size of these injections may change depending on a variety of factors. The treatment of diabetes with regular insulin injections is an example of such a disease condition and corresponding therapeutic scheme; different volumes of insulin injections are required depending upon, among other factors, blood glucose level.

SUMMARY OF THE DISCLOSURE

It is therefore an object of an embodiment of the instant invention to provide a method and apparatus that obviates, for practical purposes, the above-mentioned limitations.

A needle-less injector may include an adjustment switch in mechanical contact with a driver. The adjustment switch may be configured such that one can displace the switch to expel air or gas contained in the needle-less injector prior to administration of a needle-less injection. The adjustment switch may include a portion that is disposed within an adjustment slot configured in the housing of a needle-less injector. The adjustment switch may be moved along the adjustment slot to correspondingly displace the driver of the needle-less injector toward the dispensing end thereof. This displacement of the driver may expel air or gas from that portion of the needle-less injector that contains the injectable product. Alternatively or additionally, displacement of the driver may expel at least a portion of the injectable product from the needle-less injector. This may be particularly advantageous when one wishes to reduce the volume of the injectable product that will be injected with the needle-less injector.

BRIEF DESCRIPTION OF THE DRAWINGS

FIG. 1 illustrates a needle-less injector with an adjustment switch in accordance with an embodiment of the instant invention.

FIG. 2 illustrates the adjustment of contents of a needle-less injector with an adjustment switch in cross section, in accordance with an embodiment of the instant invention.

FIG. 3 illustrates an adjustment switch in accordance with an embodiment of the instant invention.

FIG. 4 illustrates a clamp adjustment switch in accordance with an embodiment of the instant invention. FIG. 4a depicts an outer perspective view of the clamp adjustment switch. FIG. 4b depicts an inner perspective view of the clamp adjustment switch. FIG. 4c depicts an axial cross-sectional view of the clamp adjustment switch. FIG. 4d depicts a side elevational view of the same clamp adjustment switch.

FIG. 5 illustrates a sleeve adjustment switch in accordance with an embodiment of the instant invention.

FIG. 7a depicts a driver with a member receiving indentation configured as a groove that circumscribes the driver. FIG. 7b depicts a driver with a member receiving indentation configured as a cylindrical collar that circumscribes the driver. FIG. 7c depicts a driver with a member receiving indentation configured as a cylindrical collar without a rear rim.

FIG. 8a depicts a linear adjustment slot. FIG. 8b depicts a linear adjustment slot with semi-circumferential slots in mechanical communication with the linear adjustment slot, and which are arranged perpendicularly to the linear adjustment slot and spaced equidistant from one another. FIG. 8c depicts a linear adjustment slot with graduations indicating a volume of the product section of the needle-less injector.

FIG. 9 illustrates the operation of a needle-less injector with a sleeve adjustment switch in cross section, in accordance with an embodiment of the instant invention. The sleeve adjustment switch includes two transecting members, and the housing of the needle-less injector includes two adjustment slots, accordingly. FIG. 9c further depicts the expulsion of a volume of injectable product from the needle-less injector by displacement of the sleeve adjustment switch.

FIG. 10a is a side perspective view, FIG. 10b is a side cross-sectional view and FIG. 10c is an axial perspective view.

FIG. 11a is a side perspective view, FIG. 11b is a side cross-sectional view, FIG. 11c is a plunger end perspective view and FIG. 11d is an opposite end perspective view.

DETAILED DESCRIPTION OF THE PREFERRED EMBODIMENTS

Embodiments of the present invention may be used to adjust the contents of a needle-less injector by: (1) removing air or gas contained in that portion of a needle-less injector that also contains an injectable product; (2) expelling at least a portion of the injectable product itself; or (3) a combination of the two. This is generally accomplished by displacing an internal mechanism of the needle-less injector in the direction of the dispensing end thereof, prior to actuating the needle-less injector. Any internal mechanism or combination of internal mechanisms of a needle-less injector may be displaced to effect the adjustment of contents contemplated by the present invention. In preferred embodiments, the driver of the needle-less injector is among the internal mechanisms that are displaced to adjust the contents of the needle-less injector; however, depending upon the internal configuration of a particular needle-less injector, different mechanisms may be displaced to achieve the same result.

As used herein, "injectable products" may include, but are in no way limited to, any liquids, solutions, suspensions, mixtures, diluents, reagents, solvents (e.g., for mixing with a lyophilized product to create an injectable solution), emulsions, pharmaceutical vehicles or excipients, vaccines, injectable medications, drugs, pharmaceutical agents, nucleotide based (e.g., DNA, RNA) medications, saline solution, non-medicinal fluids administered as a placebo in a clinical study, or other fluids suitable for administration with a needle-less injection. In various embodiments, the injectable product of the present invention may contain a gas, such as a dissolved gas.

In one embodiment of the instant invention, the injectable product is degassed prior to being filled into a needle-less injector such as by any of the methods described in U.S. patent application Ser. No. 09/808,511, filed Mar. 14, 2001, which is incorporated by reference herein in its entirety. It will be recognized by those of skill in the art that such degassing techniques are not practical or possible in certain instances (e.g., where the chemical composition of an injectable product renders it unsuitable for degassing). Moreover, while such degassing techniques may substantially reduce the amount of air or gas that develops in a needle-less injector, some undesirable volume of air or gas may nonetheless develop therein.

Figure 1A:
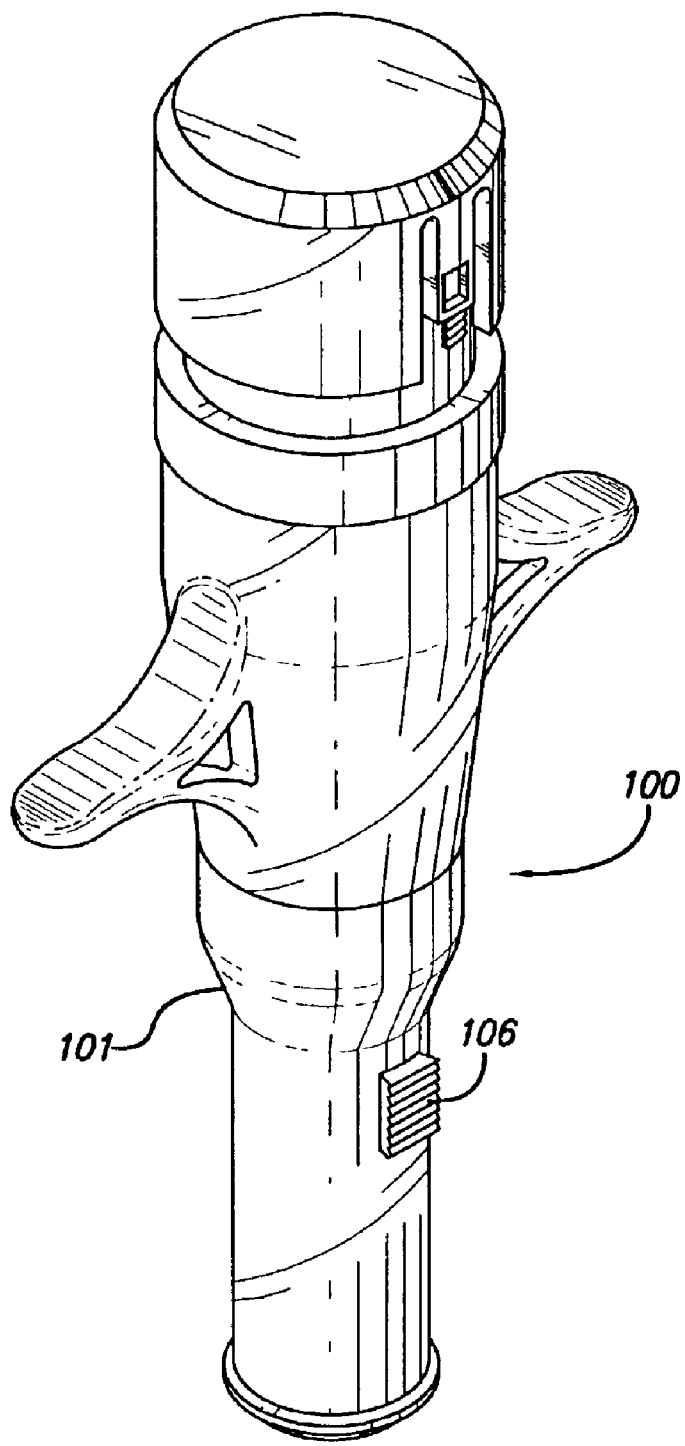
FIG. 1a is a side perspective view of an exterior of the needle-less injector including an adjustment switch.
Figure 1B:
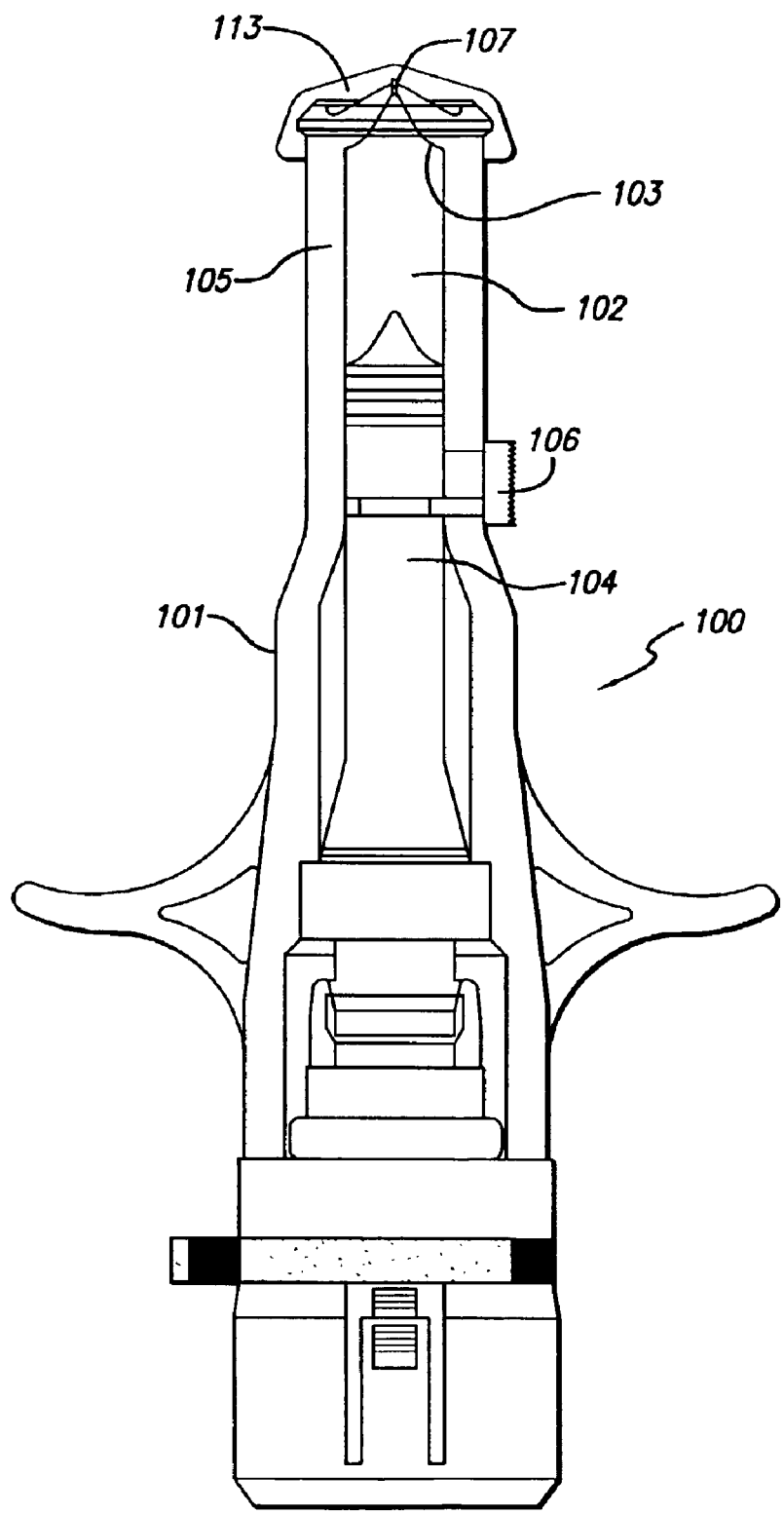
FIG. 1b is a cross-sectional view of the same needle-less injector, including a cap.

As depicted in FIG. 1, a needle-less injector 100 (or an ampoule adapted for use with a needle-less injector; hereinafter included within the term "needle-less injector") includes a housing 101 with a product section 102. The product section 102 is that portion of the needle-less injector 100 in which an injectable product is contained. It is also the portion in which a pocket of air or gas may develop or be included. With reference to FIG. 1b, the product section 102 is preferably bounded by the dispensing end 103 of the housing 101 at one end, a driver 104 at the opposing end, and the wall 105 of the housing 101 therebetween. A cap 113 may be included on the dispensing end 103 of the housing 101 to cover an orifice 107.

An adjustment switch 106 may be disposed on the exterior of the wall 105 of the needle-less injector housing 101 (FIG. 1). The adjustment switch 106 may be displaced to adjust the contents of the needle-less injector 100, such as by expelling an amount of air or gas 201 and/or injectable product 202 from the product section 102, through the orifice 107 of the needle-less injector 100. In general, as illustratively depicted in FIG. 2, this may be accomplished by displacing the adjustment switch 106 in the axial direction of the dispensing end 103 of the needle-less injector 100 (i.e., toward the orifice 107), thereby causing the driver 104 to move in the same direction.

As depicted in FIG. 3, the adjustment switch 106 is preferably of a suitable configuration to accommodate a user's finger (herein used to include the thumb), and may further include a non-slip surface 301 to aid in maintaining the interaction between a user's finger and the switch. This may be especially useful in those embodiments where a substantial amount of force is required to displace the adjustment switch 106. Furthermore, the adjustment switch 106 is preferably of a suitable size and shape to entirely cover the adjustment slot 112 before, during and after displacement of the switch. This may aid in maintaining the sterility of the adjustment slot 112 and the interior of the needle-less injector 100, since covering the adjustment slot 112 may prevent particles from clogging or otherwise blocking the movement of the adjustment switch 106.

Figure 4E:
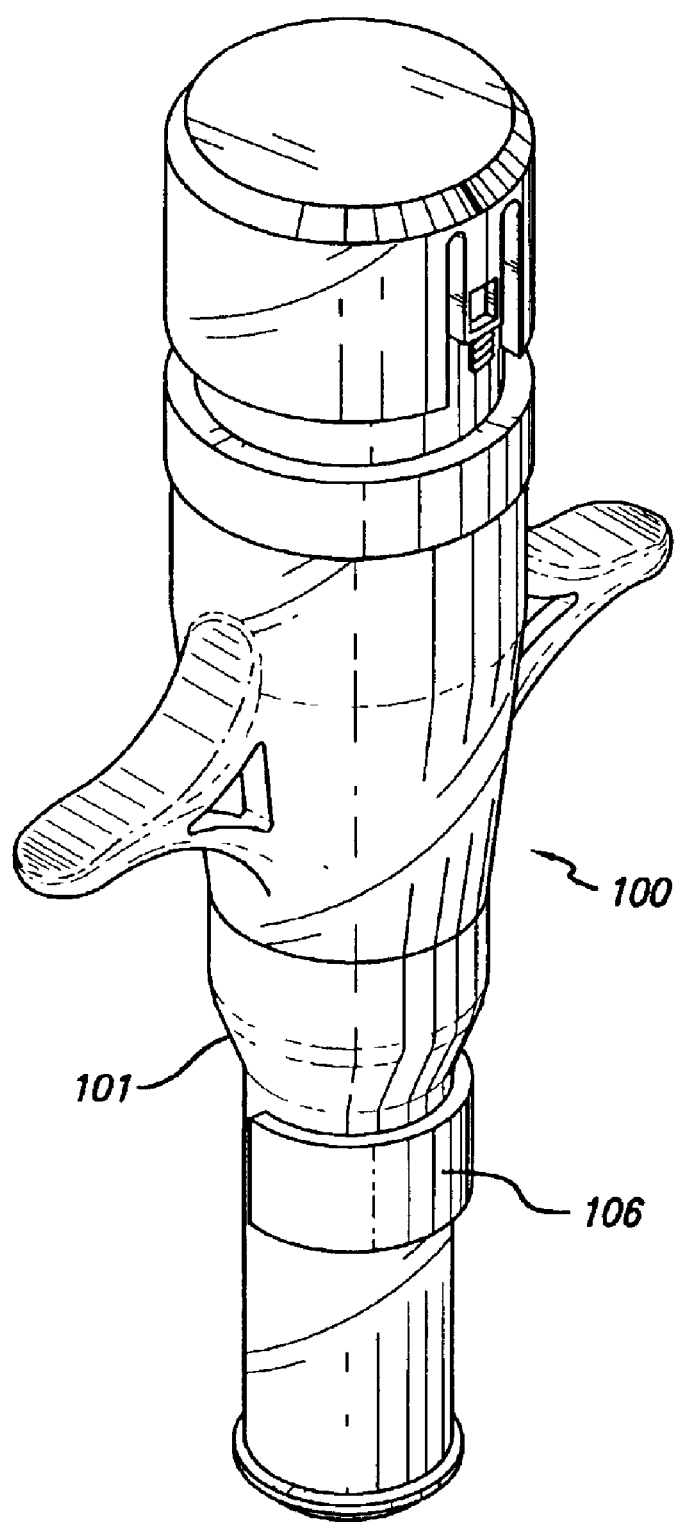
FIG. 4e depicts a side perspective view of an exterior of a needle-less injector including the clamp adjustment switch.

Various configurations for an adjustment switch 106 are depicted in FIGS. 3, 4 and 5. The adjustment switch 106 may resemble the switch on a flashlight (FIG. 3), or it may partially (FIG. 4) or entirely (FIG. 5) wrap around the exterior of the needle-less injector 100; although other configurations may be desirable and are contemplated as being within the scope of the present invention. In those embodiments wherein the adjustment switch 106 resembles the switch on a flashlight (FIG. 3), the underside 302 of the adjustment switch 106 may be a curved surface that approximately matches the curve of the wall 105 of the housing 101. This may be especially advantageous in those embodiments wherein the housing 101 of the needle-less injector 100 is cylindrical in shape.

In those embodiments wherein the adjustment switch 106 partially or entirely wraps around the exterior of the needle-less injector 100, the adjustment switch 106 may include multiple transecting members 109, as described below. Including multiple transecting members 109 may provide additional stability to a clamp (FIG. 4) or sleeve (FIG. 5) adjustment switch 106 as a user displaces the same to adjust the contents of the product section 102 of a needle-less injector 100, and may reduce or eliminate the friction between the adjustment switch 106 and the exterior of the housing 101. Moreover, the inclusion of multiple transecting members 109 may partially or entirely alleviate the creation of torsional force caused by displacement of the adjustment switch 106. In those embodiments wherein one transecting member 109 is included, or wherein a number of transecting members 109 are included but are unevenly configured about the axis of the driver 104, axial movement of the adjustment switch 106 may result in a torque being created that hampers the forward movement of the driver 104 and/or necessitates a greater amount of force from a user to move the adjustment switch 106.

Figure 5A:
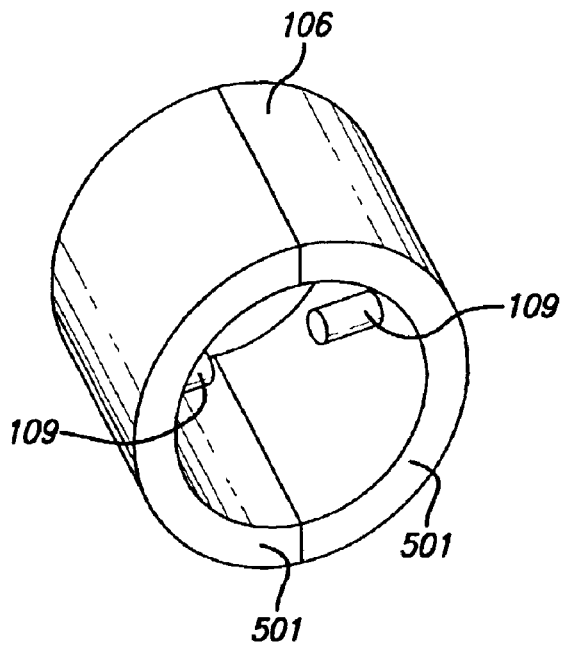
FIG. 5a depicts an axial perspective view of the sleeve adjustment switch.
Figure 5B:
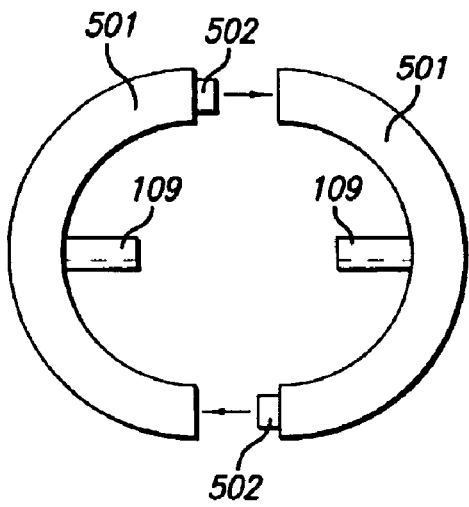
FIG. 5b depicts an axial cross-sectional view of two semi-cylindrical components of a sleeve adjustment switch.
Figure 5C:
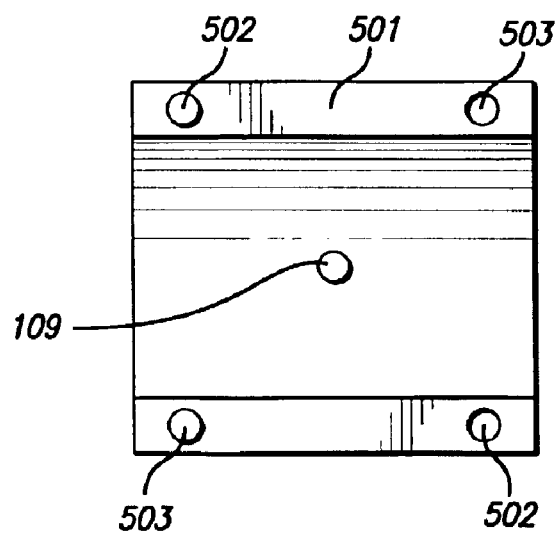
FIG. 5c depicts a side elevational view of one semi-cylindrical component of the sleeve adjustment switch.
Figure 5D:
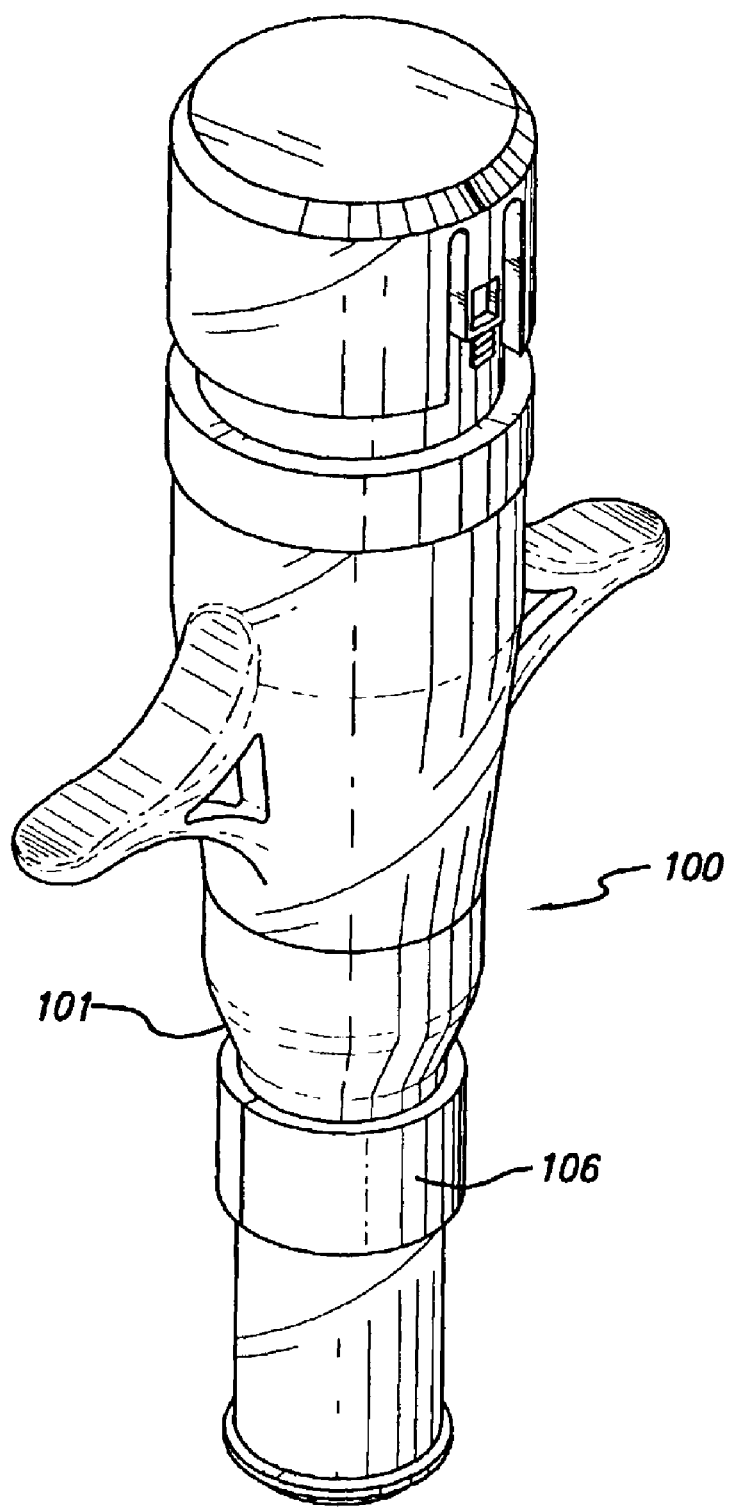
FIG. 5d depicts a side perspective view of an exterior of a needle-less injector including the sleeve adjustment switch.

A sleeve adjustment switch 106 may be composed of two semi-cylindrical components 501 that interlock, as depicted in FIG. 5b. In a preferred embodiment, the two-semi-cylindrical components 501 are identical to one another; although in alternate embodiments the semi-cylindrical components 501 may be configured in a non-identical fashion. Interlocking members 502 may be included in at least one of the corners of the semi-cylindrical component 501, and, preferably, two interlocking members 502 are included on either the upper left and lower right corners of the semi-cylindrical component 501 (FIG. 5c), or on the lower left and upper right corners of the semi-cylindrical component 501 (not shown). Correspondingly, the opposite corners of the semi-cylindrical component 501 may include an interlocking hole 503 to receive and couple with the interlocking member 502. In the semi-cylindrical component 501 depicted in FIG. 5b, two interlocking holes 503 are included on the upper right and lower left corners thereof. Other mechanisms may be utilized to couple the semi-cylindrical components 501 to one another, including alternate mechanical fittings, welding techniques, or other mechanisms that will be readily recognized to those of skill in the art.

In those embodiments wherein the adjustment switch 106 is a sleeve adjustment switch, the friction between the adjustment switch 106 and the housing 101 may be eliminated, since the interior diameter of the sleeve adjustment switch 106 may be greater than the exterior diameter of the needle-less injector housing 101. Therefore, the adjustment switch 106 may be displaced without contacting the housing 101; thereby obviating the need to overcome resistance to movement owing to friction between the sleeve adjustment switch 106 and the housing 101 of the needle-less injector 100.

The adjustment switch 106 may be permanently or removably coupled to the housing 101 of the needle-less injector 100. A removable connection allows a user to, for example, connect the adjustment switch 106 to the needle-less injector 100 and adjust the contents of the product section 102 thereof. Once the contents are adjusted, the user may then remove the adjustment switch 106 from the needle-less injector 100, and thereafter administer an injection. However, in those embodiments wherein the connection between the adjustment switch 106 and the housing 101 is permanent, the adjustment switch 106 may remain coupled to the housing 101 during the administration of an injection.

Figure 6:
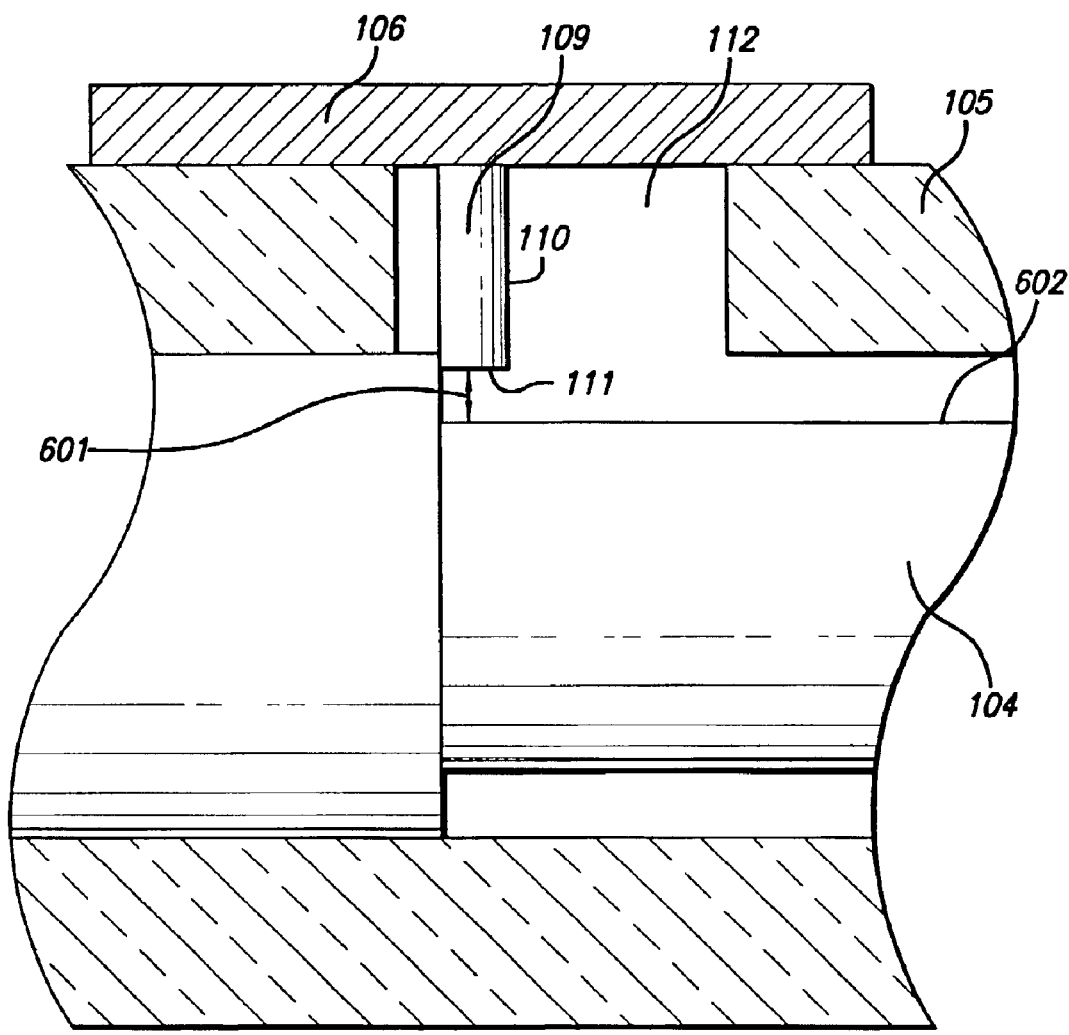
FIG. 6 illustrates a cross-sectional view of the interaction between a transecting member of an adjustment switch and a driver of a needle-less injector, in accordance with an embodiment of the instant invention.

The adjustment switch 106 may further include a transecting member 109 to provide mechanical contact between the adjustment switch 106 and the driver 104. In preferred embodiments of the present invention, the transecting member 109 is only in contact with the driver 104 on its side 110, and not on its end 111 (FIG. 6). A space 601 is preferably included between the end 111 of the transecting member 109 and the member receiving indentation 602. This may allow the driver 104 to glide by the transecting member 109 during the administration of a needle-less injection.

Figure 7A:
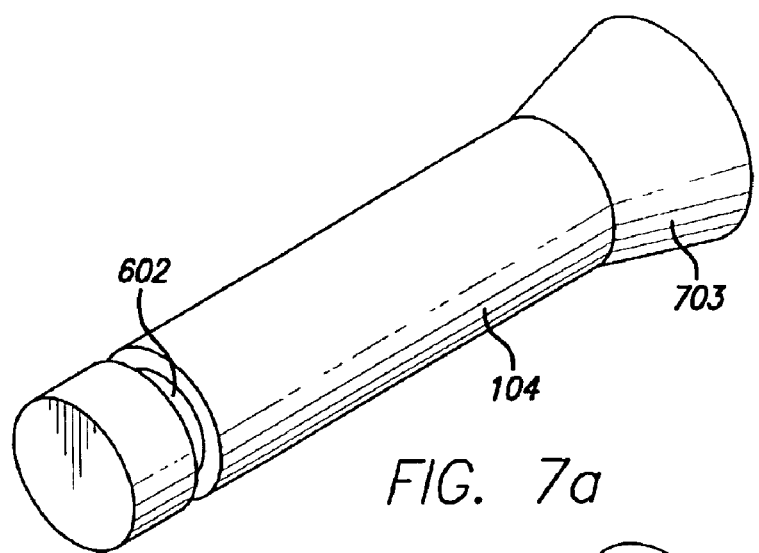
FIGS. 7a–c illustrate several embodiments of a member receiving indentation configured on the driver of a needle-less injector, in accordance with various embodiments of the instant invention.

To accommodate the connection between the transecting member 109 and the driver 104, the driver 104 may include a member receiving indentation 602. Depending upon the cross-sectional configuration of the driver 104, which, in alternate embodiments, may be cylindrical, triangular, or any other suitable shape, the member receiving indentation 602 may either partially or completely circumscribe (i.e., go all the way around) the driver 104. In a first embodiment illustratively depicted in FIG. 7a, the driver 104 is cylindrical in shape, and the member receiving indentation 602 is a groove that circumscribes the driver 104. In still further embodiments, the member receiving indentation 602 may be a single depression or "dimple" in the driver 104 (not shown), rather than a depression akin to the groove depicted in FIG. 7a.

Figure 7B:
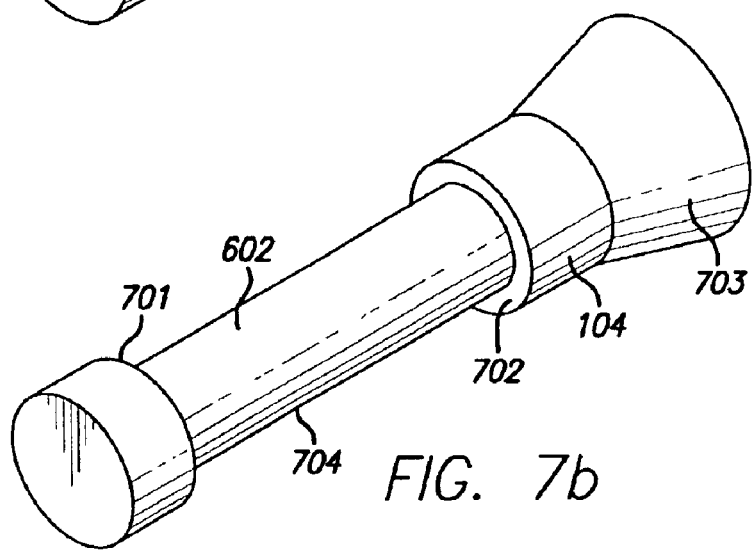
Figure 7C:
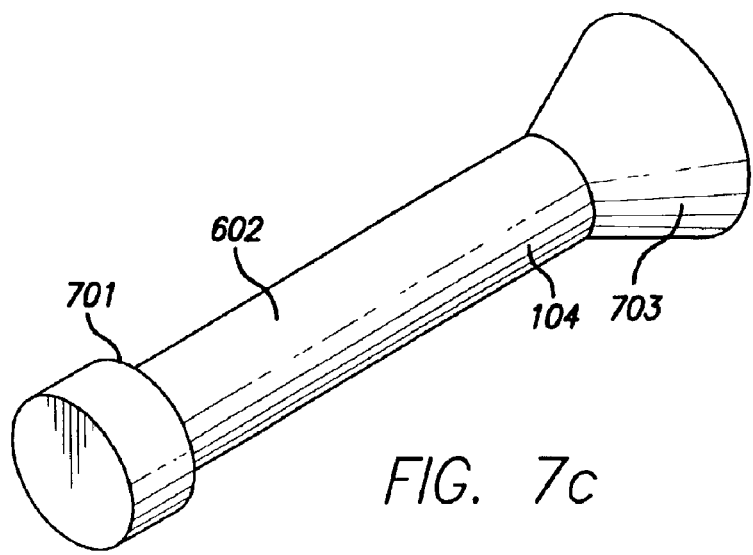

In an alternate embodiment, depicted in FIG. 7b, the member receiving indentation 602 is a cylindrical collar 704. In a preferred embodiment, the cylindrical collar 704 is of at least an "injection length" along the axis of the driver 104 terminating at one end at a forward rim 701, at the opposing end at a rear rim 702, and circumscribing the driver 104. An injection length is the distance which a driver 104 is displaced during administration of a needle-less injection plus the width of the transecting member 109. Configuring the cylindrical collar 704 at a length at least as long as the injection length allows the adjustment switch 106 to be used to adjust the contents of the needle-less injector 100, but to thereafter remain connected to the housing 101 of the needle-less injector 100 without interfering with the administration of an injection therewith. In a most preferred embodiment, the cylindrical collar 704 does not include a rear rim 702 at all; rather, the cylindrical collar 704 tapers into a flared segment 703 of the driver 104 (FIG. 7c).

In embodiments wherein the member receiving indentation 602 is a cylindrical collar 704, the transecting member 109 may abut the forward rim 701 of the cylindrical collar 704, such that by moving the transecting member 109 in the axial direction of the orifice 107 of the needle-less injector 100, the driver 104 is displaced as well. Reverse motion of the transecting member 109 in this embodiment preferably does not affect the position of the driver 104, since the driver 104 preferably does not include any mechanical element with which to engage the transecting member 109 when the transecting member 109 is displaced in the reverse direction. Similarly, if the driver 104 of the needle-less injector 100 is displaced in the axial direction of the orifice 107 (e.g., during administration of a needle-less injection), then the driver 104 does not effect a movement of the transecting member 109 (or the adjustment switch 106), since the driver 104 does not have any mechanical element with which to engage the transecting member 109 when displaced in that direction, until the transecting member 109 comes into contact with the rear rim 702 of the cylindrical collar 704. Preferably, the transecting member 109 does not come into contact with the rear rim 702 until the driver 104 has completed its movement toward the dispensing end 103 of the needle-less injector 100 (i.e., the injection is complete). Alternatively, the transecting member 109 does not mechanically contact the rear rim 702 at any time prior to, during or after adjusting the contents of, or administering an injection with, a needle-less injector 100. Moreover, in a most preferred embodiment, the cylindrical collar 704 does not include a rear rim 702 (FIG. 7c).

In embodiments of the instant invention wherein the member receiving indentation 602 is a cylindrical collar 704, if the driver 104 of the needle-less injector 100 is displaced in the axial direction opposite the orifice 107 (e.g., during the filling of a needle-less injector), then the driver 104 does not effect a movement of the transecting member 109 (or the adjustment switch 106), since the driver 104 does not have any mechanical element with which to engage the transecting member 109 when displaced in that direction, until the transecting member 109 comes into contact with the forward rim 701 of the cylindrical collar 704. Preferably, the transecting member 109 does not come into contact with the forward rim 701 until the driver 104 has completed its movement away from the dispensing end 103 of the needle-less injector 100 (i.e., the filling operation is complete).

Figure 8A:
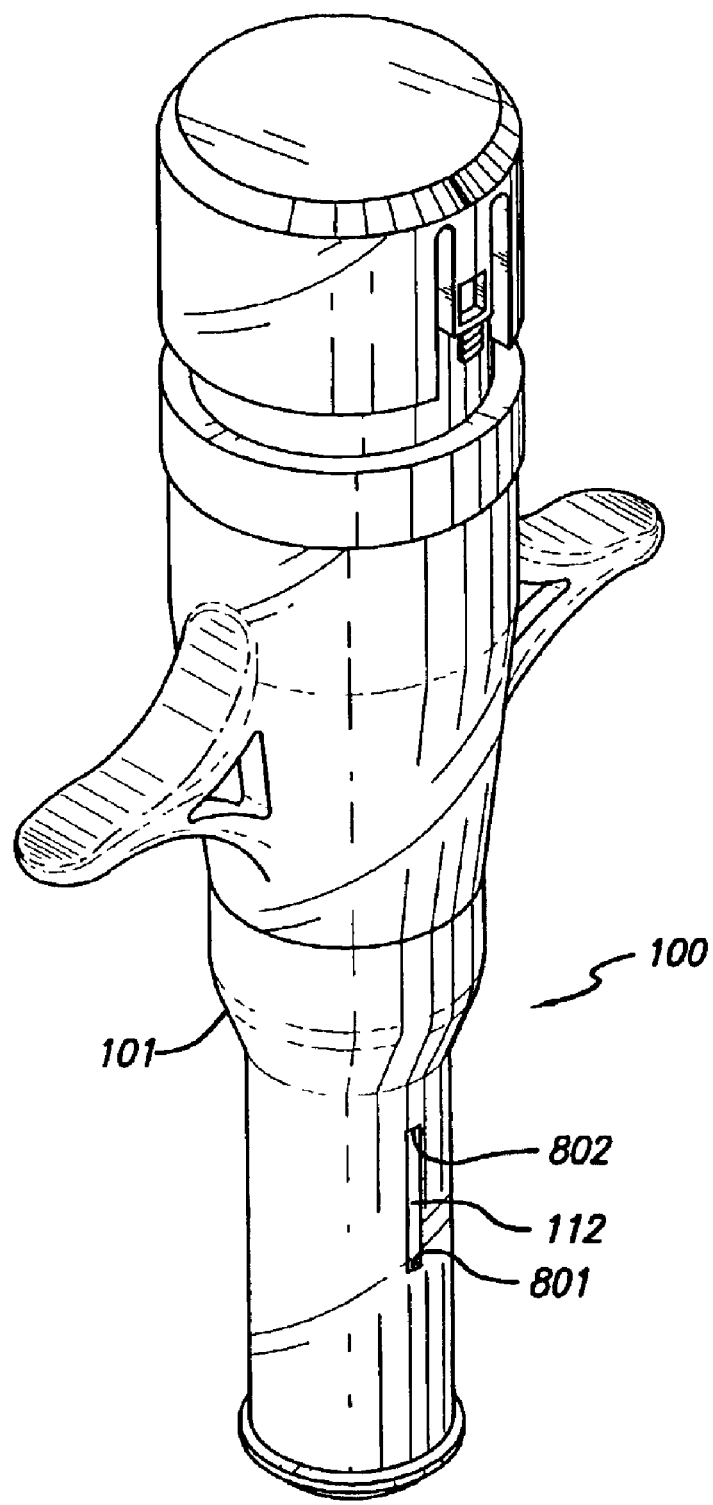
FIGS. 8a–c illustrate several embodiments of an adjustment slot configured through the housing of a needle-less injector, in accordance with various embodiments of the instant invention.

As depicted in FIG. 8, the wall 105 of the housing 101 may include an adjustment slot 112 through which the transecting member 109 is disposed such that it may mechanically connect the adjustment switch 109 to the driver 104. In one embodiment (FIG. 8a), the adjustment slot 112 may be linear, and may have two ends: a forward terminus 801 and a rear terminus 802. In a preferred embodiment, the forward terminus 801 of the adjustment slot 112 is disposed at a position in the housing 101 "behind" the end of the driver 104 that defines the product section 102 of the needle-less injector 100. In other words, the adjustment slot 112 preferably does not extend beyond the end of the driver 104 that defines the boundary of the product section 102. In this configuration, the injectable product 202 contained within the product section 102 does not leak out through the adjustment slot 112. In a most preferred embodiment, the forward terminus 801 of the adjustment slot 112 is disposed at a position in the housing 101 "behind" an element of the driver 104 that provides a fluid-tight seal with respect to the injectable product 202. By configuring the adjustment slot 112 and driver 104 in this fashion, the integrity of the product section 102 of the housing 101 may be preserved; thereby maintaining the sterility of the injectable product 202 in the product section 102. In a most preferred embodiment of the present invention, as described in greater detail below, the driver 104 includes both a piston 1100 and a plunger 1000, and the forward terminus 801 of the adjustment slot 112 is disposed at a position in the housing 101 that, in all instances (e.g., during a filling operation, during storage of the needle-less injector 100 with a pre-filled injectable product 202, and during administration of an injection), is "behind" the location of the plunger 1000.

Figure 8B:
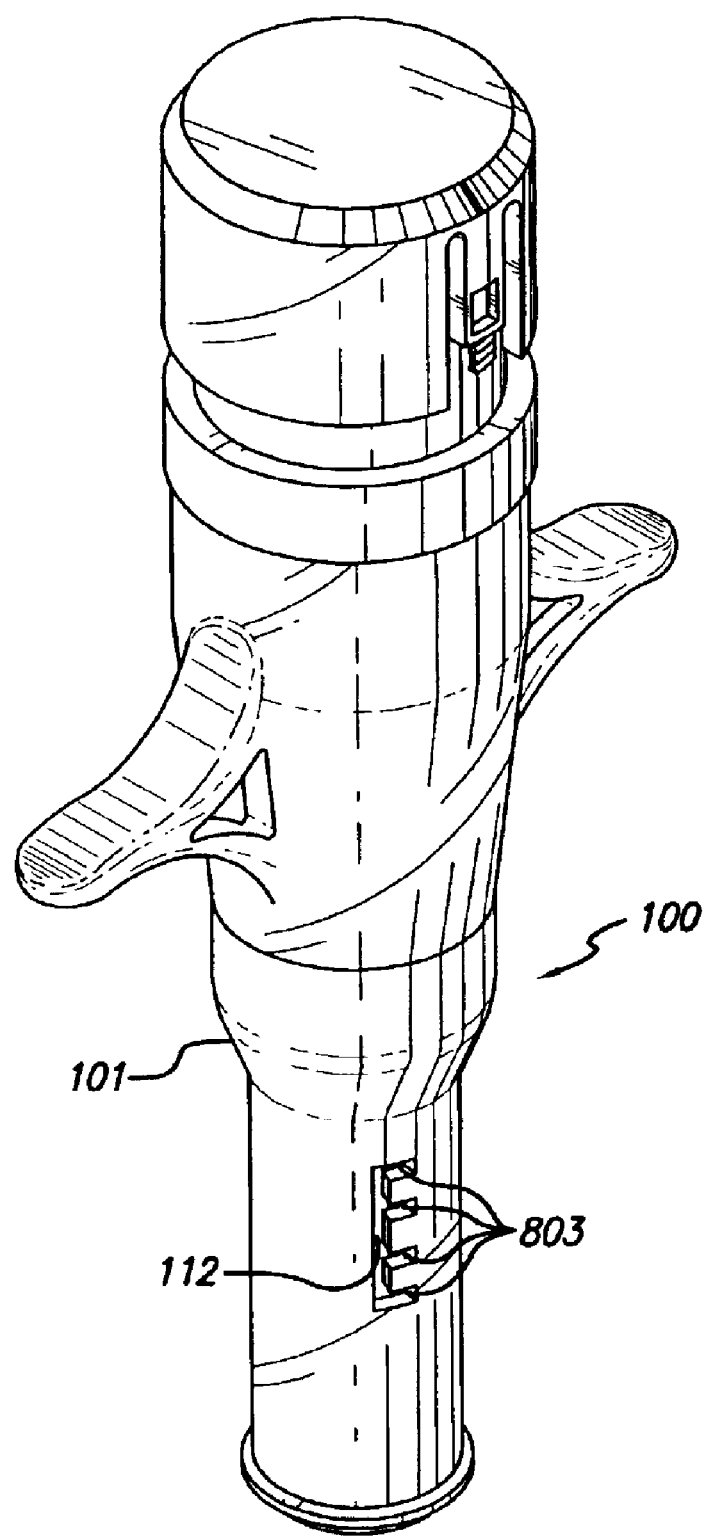
Figure 8C:
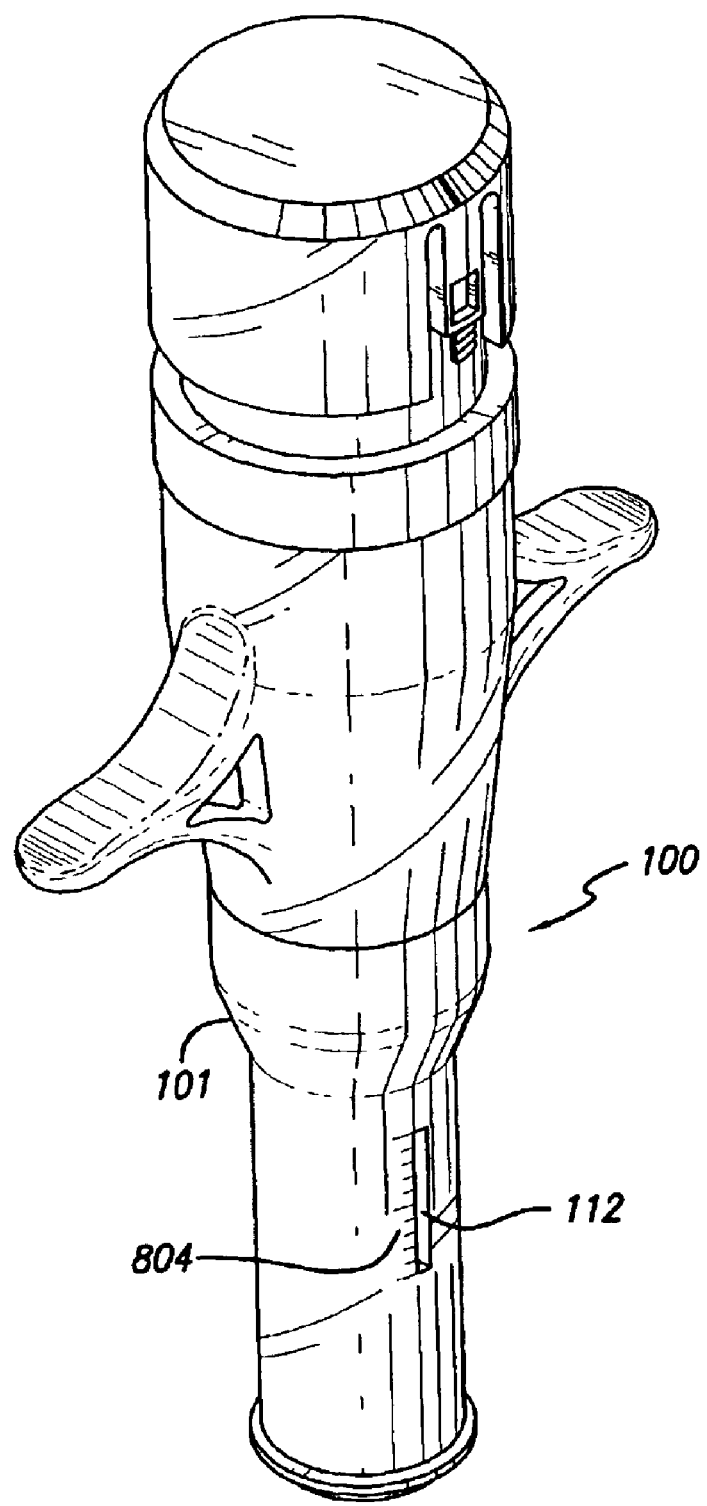

Graduations 804 may be included on the housing 101 of the needle-less injector 100 to indicate when an appropriate adjustment position has been achieved (FIG. 8c). In an alternate embodiment (FIG. 8b), the adjustment slot 112 may include a number of semi-circumferential slots 803 configured approximately perpendicular to the adjustment slot 112. The semi-circumferential slots 803 may be positioned at any desirable distance from one another, and in a preferred embodiment, the semi-circumferential slots 803 are positioned equidistant from one another. In this embodiment of the present invention, the adjustment switch 106 may be displaced similar to a gear shift in an automobile; the adjustment switch 106 being moved along the adjustment slot 112 until it reaches an appropriate semi-circumferential slot 803 into which the transecting member 109 may be positioned by rotating the adjustment switch 106 about the housing 101 of the needle-less injector 100. Such a configuration may allow a user to adjust the contents of the product section 102 with the added mechanical satisfaction of "shifting" the adjustment switch 106 into an appropriate position; indicating to the user that an appropriate adjustment position has been achieved. Other configurations for the adjustment slot 112 may be included on the housing 101. For instance, the semi-circumferential slots 803 may be disposed on alternating sides of the adjustment slot 112 (not shown) as opposed to being disposed entirely on one side of the adjustment slot 112 (FIG. 8b). Alternatively, the adjustment slot 112 may be a non-linear "zig-zag" shape (not shown), including segments that run parallel to the central axis of the needle-less injector 100 interspersed with segments that are perpendicular to the central axis of the needle-less injector 190. Each of these alternative embodiments are contemplated as being within the scope of the present invention, as are still further embodiments of the adjustment slot 112 that may be desirable.

Moreover, multiple adjustment slots 112 may be included in the housing 101 of the needle-less injector 100 to accommodate a corresponding number of transecting members 109 included on an adjustment switch 106. For example, in one embodiment of the present invention, illustratively depicted in FIG. 9, an adjustment switch 106 includes two transecting members disposed 180° apart from one another. Correspondingly, the housing 101 may include two adjustment slots also disposed 180° apart from one another. In still further embodiments, additional transecting members and/or adjustment slots may be included in the housing 101 of a needle-less injector 100. The number of transecting members need not be the same as the number of adjustment slots.

The length of the adjustment slot 112 may be of a "maximum adjustment length," a "complete injection length," or any other suitable length. A "maximum adjustment length" is that distance which the driver 104 of the needle-less injector 100 is moved to effect the discharge of the maximum desirable volume of air or gas 201 from the needle-less injector 100. To ensure that the maximum desirable volume or air or gas 201 is expelled from the needle-less injector 100, a small quantity of injectable product 202 may be expelled as well. The maximum adjustment length may be calculated as the maximum volume of air or gas 201 and/or injectable product 202 that one may discharge from a needle-less injector 100 to adjust the contents thereof, divided by the average cross-sectional area of the product section 102 of the housing 101. Configuring the adjustment slot 112 at the maximum adjustment length may be particularly desirable in those embodiments wherein the size of an air or gas bubble 201 that develops in the product section 102 can be predetermined. If the size of the bubble is known, one can configure the adjustment slot 112 at an appropriate "maximum adjustment" length, such that a user may expel the air or gas bubble 201 prior to administration of a needle-less injection. There are other instances in which it may be desirable to configure the adjustment slot 112 to the maximum adjustment length, each of which is contemplated as being within the scope of the present invention.

For example, a needle-less injector 100 may be pre-filled with a 0.5 ml volume of an injectable product 202, yet an injection of only 0.4 ml of the injectable product 202 may be desired. An adjustment slot 112 may be included that allows a user to expel 0.1 ml of the injectable product 202 from the product section 102 of the needle-less injector 100 prior to administration of an injection therewith. The length required for such an adjustment with a substantially degassed injectable product 202 (i.e., one where substantially no air or gas bubble 201 develops) may be the maximum adjustment length, and an adjustment slot 112 of a maximum adjustment length may be included. A user may therefore administer a needle-less injection of either 0.5 ml or 0.4 ml by either leaving the adjustment switch 106 in its initial position, or by displacing the adjustment switch 106 through the maximum adjustment length (i.e., the point at which the transecting member 109 contacts the forward terminus 801 of the adjustment slot 112), respectively.

Figure 2A:
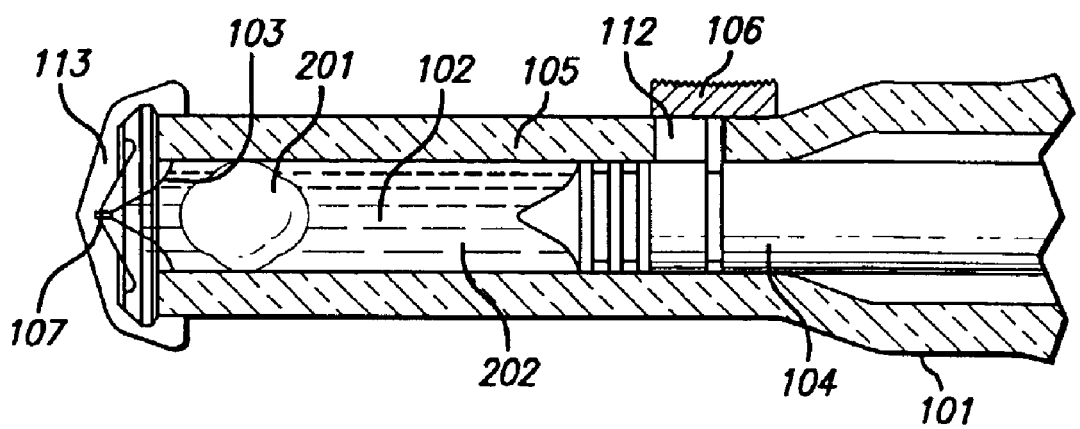
FIG. 2a depicts a needle-less injector with a cap filled with an injectable product and further including an air bubble.
Figure 2B:
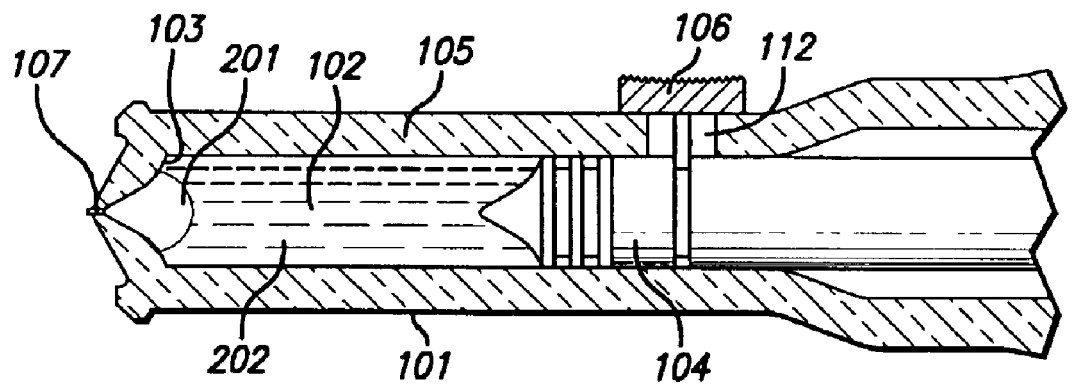
FIG. 2b depicts an expulsion of the air bubble from the needle-less injector by displacement of the adjustment switch.
Figure 2C:
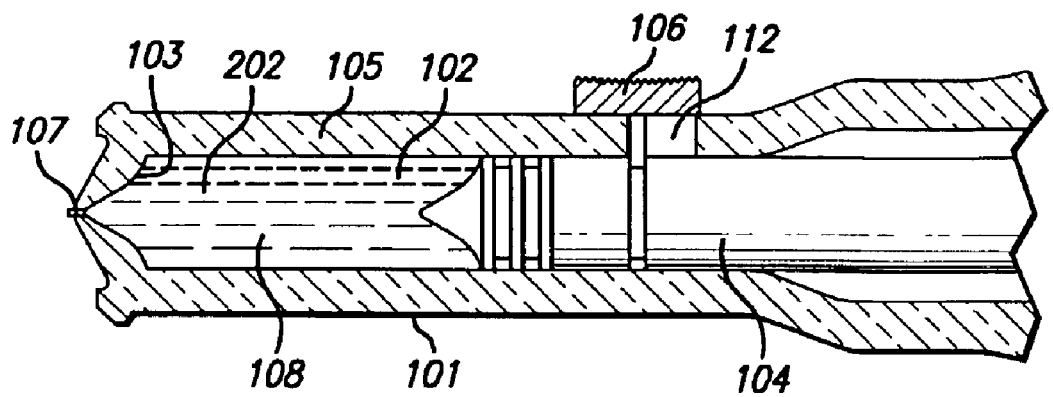
FIG. 2c depicts the same needle-less injector; the air bubble having been completely expelled by displacement of the adjustment switch.
Figure 3A:
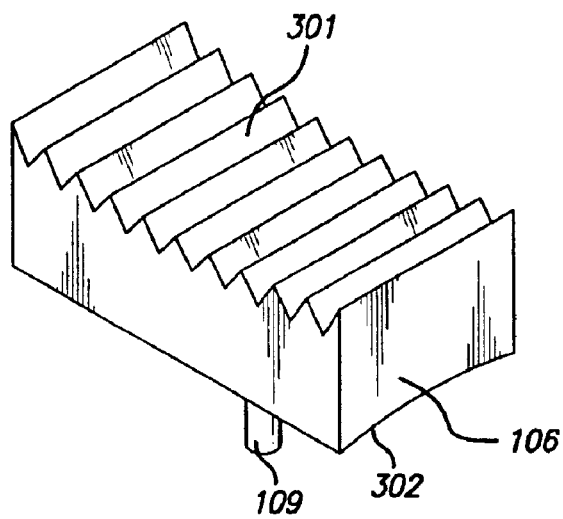
FIG. 3a depicts a top perspective view of the adjustment switch.
Figure 3B:
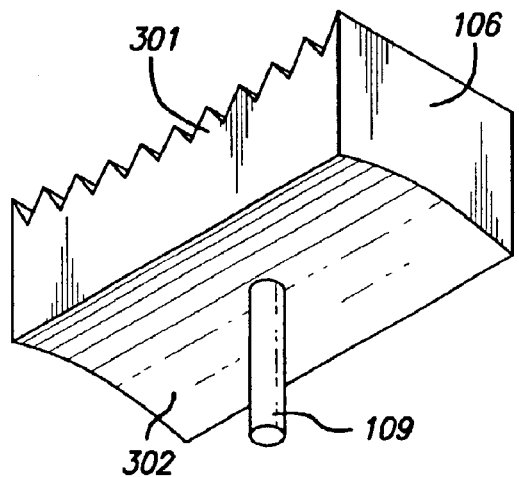
FIG. 3b depicts a bottom perspective view of the adjustment switch.
Figure 3C:
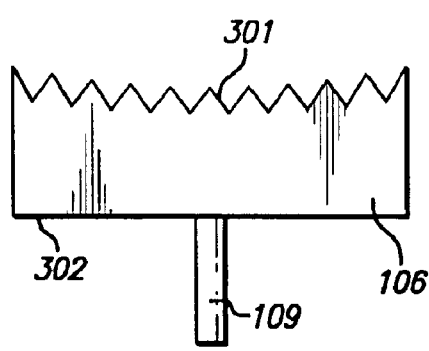
FIG. 3c depicts a side cross-sectional view of the adjustment switch.
Figure 3D:
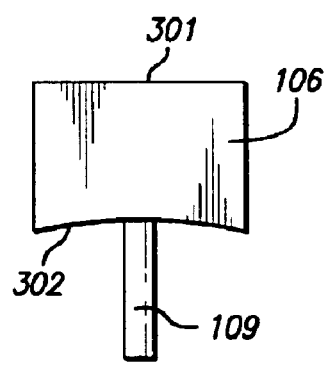
FIG. 3d depicts an axial cross-sectional view of the same adjustment switch.
Figure 9A:
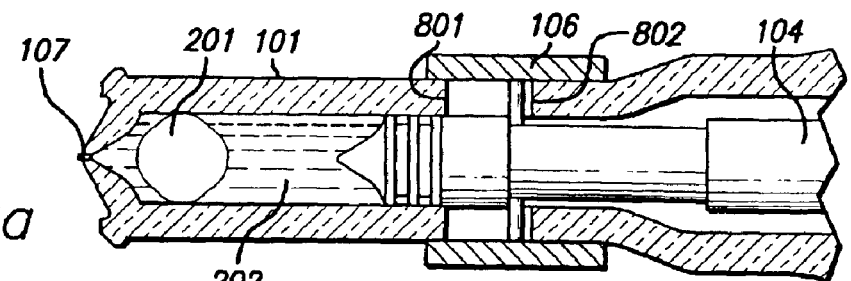
FIG. 9a depicts the needle-less injector filled with an injectable product and further including an air bubble.
Figure 9B:
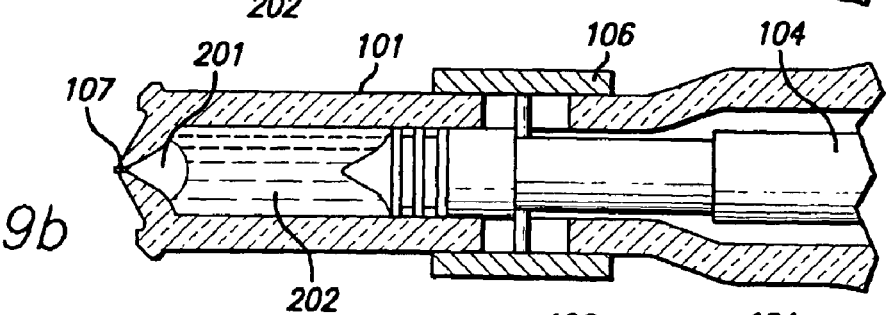
FIG. 9b depicts an expulsion of the air bubble from the needle-less injector by displacement of the sleeve adjustment switch.
Figure 9C:
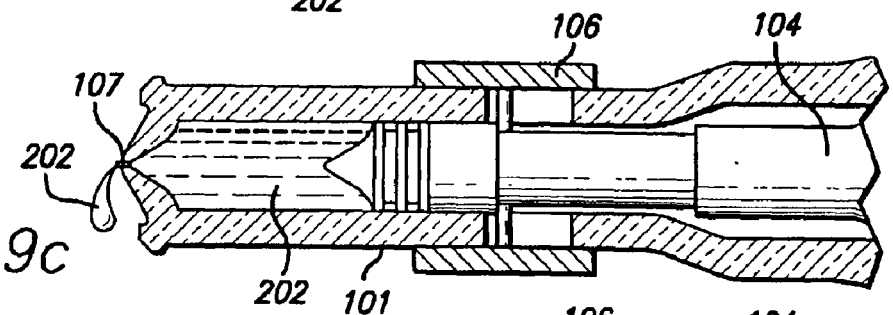
FIG. 9c depicts the same needle-less injector; the air bubble having been completely expelled by displacement of the sleeve adjustment switch.
Figure 9D:
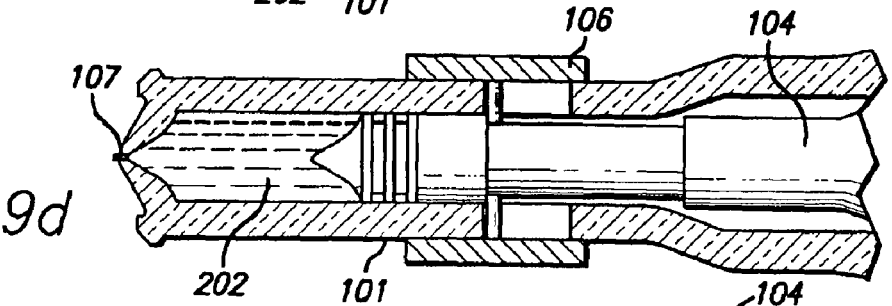
FIG. 9d depicts the same needle-less injector once the displacement of the sleeve adjustment switch is complete.

In a further example, a needle-less injector 100 may be pre-filled with a volume of an injectable product 202. Over a period of storage time, however, an amount of dissolved gas 201 may separate from the injectable product 202, leaving a reduced volume of the injectable product 202 in the product section 102 of the needle-less injector 100, along with a volume of separated gas 201 that accounts for the remainder of the internal volume of the product section 102 (i.e., a gas bubble) (FIGS. 2a & 9a). Since the volume of a gas bubble 201 that is likely to develop in a product section 102 may be predetermined (based on the chemistry of the injectable product, the storage temperature, the length of the storage period, and other factors), an adjustment slot 112 may be included that allows a user to expel a volume of the contents from the product section 102 of the needle-less injector 100 roughly equivalent to the volume of the gas bubble 201. Holding the needle-less injector 100 such that the orifice is oriented in an "up" direction, displacement of the adjustment switch 106 in the direction of the orifice may expel the gas bubble 201 from the product section 102 of the needle-less injector 100. The length required for such an adjustment may be the maximum adjustment length, and an adjustment slot 112 of a maximum adjustment length may be included. A user may therefore expel the gas bubble 201 that is of predetermined size, by displacing the adjustment switch 106 through the maximum adjustment length (i.e., the point at which the transecting member contacts the forward terminus of the adjustment slot).

A complete "injection length" is the entire distance that a driver 104 may be displaced during the administration of a needle-less injection. By configuring the adjustment slot 112 at this length, a user may adjust the contents of the product section 102, by: (1) expelling air or gas 201 that develops in the product section 102; (2) reducing the volume of injectable product 202 contained in the product section 102 (e.g., reducing the dosage of a pre-filled needle-less injector 100);

or (3) a combination thereof. In those instances where a user may utilize the adjustment switch 106 to adjust the volume of the injectable product 202, it may be desirable for the adjustment slot 106 to include semi-cylindrical slots 803 (FIG. 8b), or for the housing 101 to include graduations 804 indicative of the volume of the product section 102 (FIG. 8c). A user may then displace the adjustment switch 106 to reach a desired volume of injection, by visually referring to the graduations 804 on the housing 101.

Figure 9E:
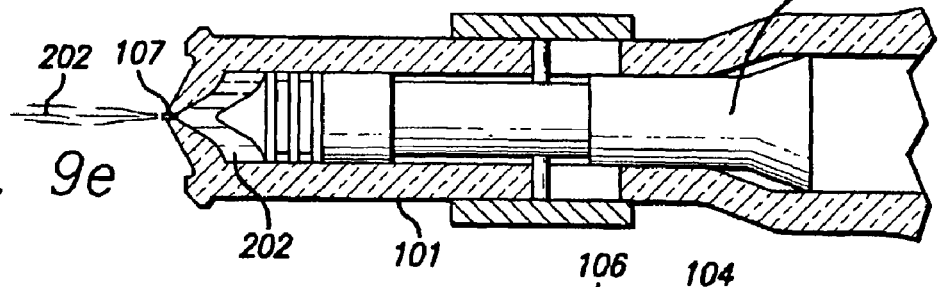
FIG. 9e depicts the same needle-less injector during administration of an injection.
Figure 9F:
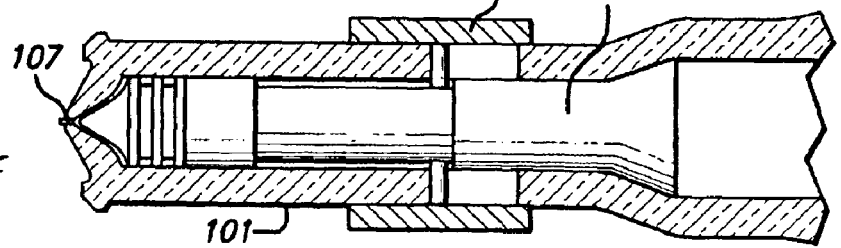
FIG. 9f depicts the same needle-less injector upon completion of an injection.

Preferably, in those embodiments wherein the adjustment slot 112 is of the maximum adjustment length, the member receiving indentation 602 is configured as a cylindrical collar 704, as depicted in FIG. 7b or 7c. This combination enables a user to adjust the contents of a needle-less injector 100 with the adjustment switch 106 by expelling, at most, the maximum adjustment volume of air or gas 201 and/or injectable product 202, and to thereafter administer a needle-less injection without the need to remove the adjustment switch 106. In practice, as illustratively depicted in FIG. 9, the adjustment switch 106 may be displaced from the rear terminus 802 of the adjustment slot 112 to the forward terminus 801 of the adjustment slot 112 (FIGS. 9a–d), or to another point between the forward terminus 802 and rear terminus 803. Displacement of the adjustment switch 106 may force an air or gas bubble 201 (FIG. 9b) and/or a volume of the injectable product 202 (FIG. 9c) out of the orifice 107 of the needle-less injector 100. The adjustment switch 106 may remain connected to the needle-less injector 100 during an administration of an injection, since the adjustment switch 106 may remain stationary as the cylindrical collar 704 of the driver 104 glides by the transecting member 109 (FIGS. 9e and 9f).

Figure 10A:
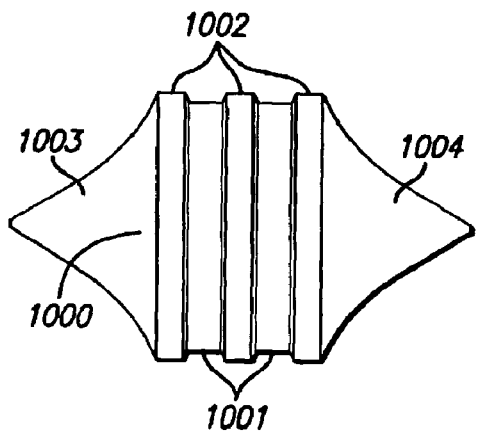
FIGS. 10a–c illustrate the plunger of a needle-less injector driver in accordance with an embodiment of the instant invention.
Figure 10B:
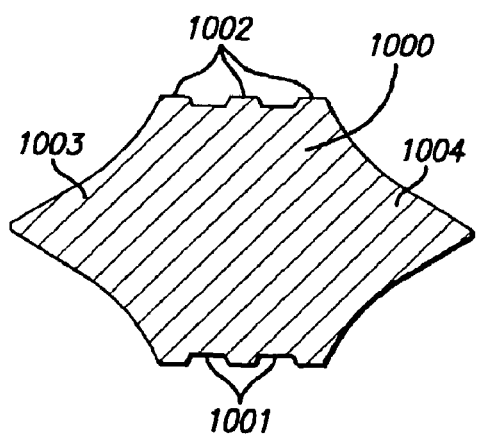
Figure 10C:
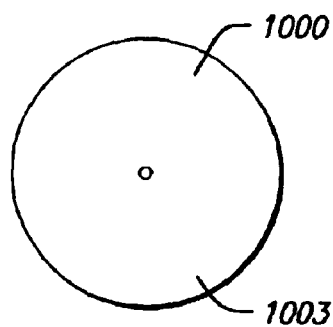
Figure 11A:
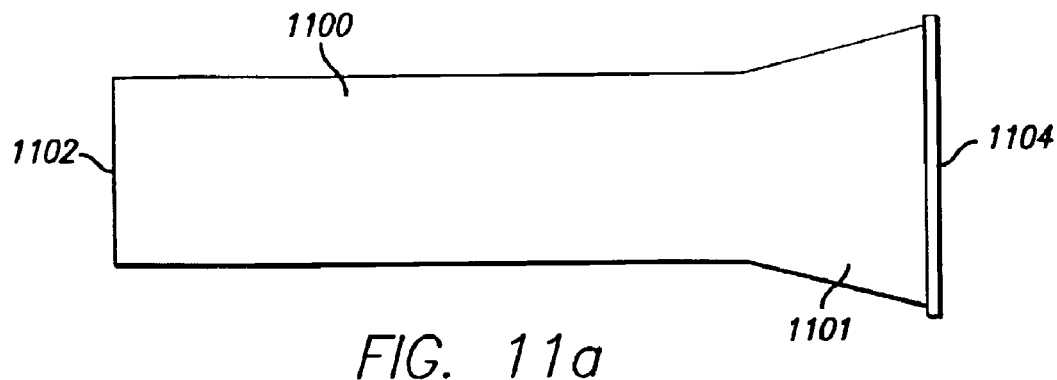
FIGS. 11a–d illustrate the piston of a needle-less injector driver in accordance with an embodiment of the instant invention.
Figure 11B:
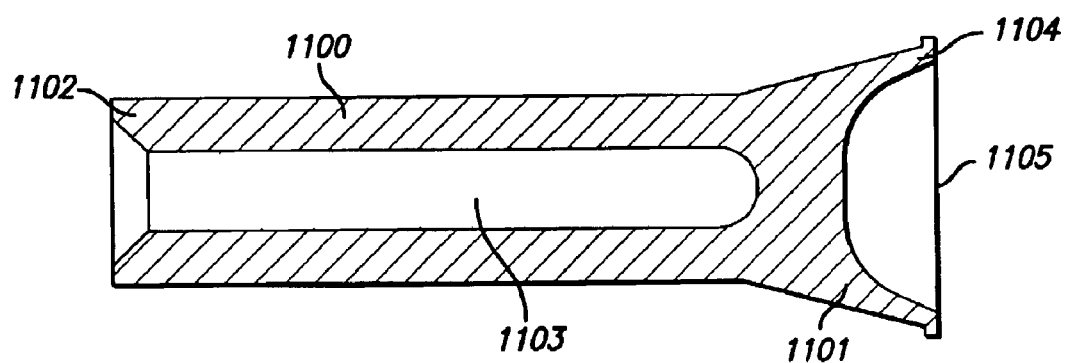
Figure 11C:
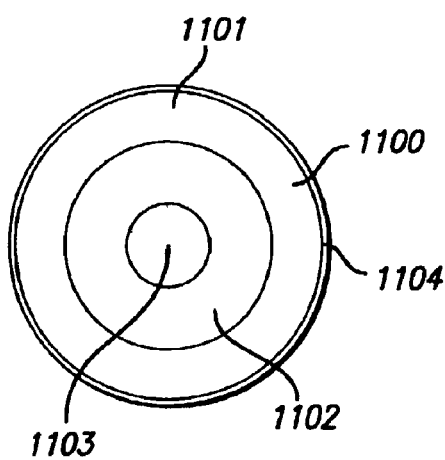
Figure 11D:
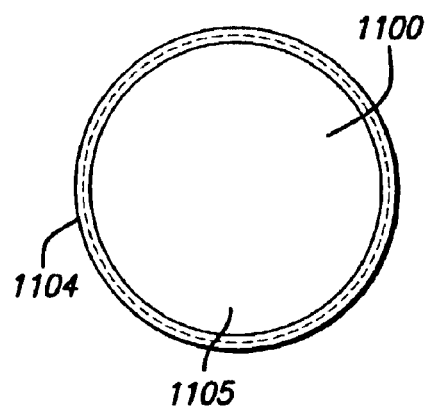

The driver may include both a plunger 1000 (FIG. 10) and a piston 1100 (FIG. 11). In preferred embodiments of the present invention, the piston 1100 is the component of the driver 104 that includes the member receiving indentation 602, while the plunger 1000 is the component of the driver 104 that provides a rear boundary of the product section 102. The distal end 1004 of the plunger 1000 may be of any suitable shape, and may be mechanically received by the proximate end 1102 of the piston 1100. In preferred embodiments, the plunger 1000 is symmetrical in shape along a plane perpendicular to its central axis. Thus, in preferred embodiments, the distal end 1004 and the proximate end 1003 of the plunger are both roughly conical in shape.

The piston 1100 preferably is of roughly cylindrical shape along the length of its central axis with a flared portion 703 toward its distal end, though other shapes may be appropriate especially in those embodiments where the wall 105 of the housing 101 is non-cylindrical. Preferably, the proximate end 1102 of the piston 1100 is shaped such that it mechanically receives the distal end 1004 of the plunger 1000. Thus, in most preferred embodiments, the proximate end 1102 of the piston 1100 is a roughly conical indentation. The flared portion 703 of the piston 1100 may terminate in an expansion cup rim 1104. In most preferred embodiments, the piston 1100 further has a hollow expansion cup 1105.

EXAMPLE

Adjusting the Contents of a Needle-Less Injector

A needle-less injector contains an injectable product, and an air bubble has developed in the product section thereof. A sleeve adjustment switch is included on the needle-less injector. A user removes a cap from the dispensing end of the needle-less injector, and, holding the needle-less injector with the dispensing end oriented in an "up" direction, the user displaces the sleeve adjustment switch until the air bubble is evacuated from the product section of the needle-less injector and a small volume of fluid begins being forced through the orifice of the needle-less injector. The user then ceases displacement of the adjustment sleeve, and administers a needle-less injection with the needle-less injector.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

We claim:

1. An apparatus for adjusting contents of a needle-less injector, comprising:

an adjustment switch to adjust said contents of said needle-less injector;

a driver to force a volume of said contents of said needle-less injector out of said needle-less injector through an orifice; and a transecting member attached to said adjustment switch, to provide mechanical interaction between said adjustment switch and said driver, wherein displacement of said adjustment switch in the direction of a dispensing end of said needle-less injector causes said driver to move toward said dispensing end of said needle-less injector.

2. The apparatus of claim 1, wherein said contents are selected from the group consisting of air, gas, an injectable product, a degassed injectable product, and combinations thereof.

3. The apparatus of claim 1, wherein said transecting member is attached to a bottom surface of said adjustment switch, and said adjustment switch includes a non-slip surface on a top surface thereof.

4. The apparatus of claim 3, wherein said bottom surface of said adjustment switch is a curved surface that substantially coincides with a curved exterior surface of said needle-less injector.

5. The apparatus of claim 1, wherein said adjustment switch is selected from the group consisting of an adjustment switch that partially wraps around said needle-less injector and an adjustment switch that entirely wraps around said needle-less injector.

6. The apparatus of claim 5, wherein said adjustment switch includes at least two transecting members.

7. The apparatus of claim 5, wherein said adjustment switch entirely wraps around said needle-less injector, and said adjustment switch includes a first semi-cylindrical component and a second semi-cylindrical component that are coupled to one another to form said adjustment switch.

8. The apparatus of claim 7, wherein said first and second semi-cylindrical components are coupled to one another by at least one set of an interlocking member on a one of said first and second semi-cylindrical components and a receiving hole on the other of said first and second semi-cylindrical components.

9. The apparatus of claim 8, wherein said first and second semi-cylindrical components are identical.

10. The apparatus of claim 1, wherein said needle-less injector includes an adjustment slot to allow said transecting member to provide mechanical interaction between said adjustment switch and said driver.

11. The apparatus of claim 10, wherein said adjustment slot includes a forward terminus disposed at a position in said housing behind an element of said driver that provides a fluid-tight seal with respect to said injectable product in said needle-less injector.

12. The apparatus of claim 10, wherein said adjustment slot is linear.

13. The apparatus of claim 10, wherein said adjustment slot includes at least one semi-circumferential slot configured approximately perpendicularly to said adjustment slot, to receive said transecting member when said adjustment switch is displaced to a point that corresponds to a particular pre-determined total volume of said contents of said needle-less injector.

14. The apparatus of claim 10, wherein said adjustment slot is configured at a length selected from the group consisting of a maximum adjustment length and a complete injection length.

15. The apparatus of claim 1, wherein said adjustment switch covers said adjustment slot.

16. The apparatus of claim 1, wherein said driver includes a member receiving indentation to allow an interaction between said transecting member and said driver.

17. The apparatus of claim 16, wherein said member receiving indentation is selected from the group consisting of a groove circumscribing said driver, a cylindrical collar having a rear rim and circumscribing said driver, a cylindrical collar without a rear rim and circumscribing said driver, and a dimple.

18. The apparatus of claim 16, further including a space between said member receiving indentation and an end of said transecting member to allow said driver to glide by said transecting member upon administration of an injection with said needle-less injector.

19. The apparatus of claim 1, wherein said driver includes a piston and a plunger.

20. A method of adjusting contents of a needle-less injector, comprising:
providing a needle-less injector, comprising
an adjustment switch to adjust said contents of said needle-less injector,
a driver to force a volume of said contents of said needle-less injector out of said needle-less injector through an orifice, and
a transecting member attached to said adjustment switch, to provide mechanical interaction between said adjustment switch and said driver,
wherein displacement of said adjustment switch in the direction of a dispensing end of said needle-less injector causes said driver to move toward said dispensing end of said needle-less injector; and
displacing said adjustment switch toward said dispensing end of said needle-less injector to cause said driver to move toward said dispensing end of said needle-less injector, thereby, forcing a volume of said contents out of said needle-less injector through said orifice.

21. The method of claim 20, wherein said contents are selected from the group consisting of air, gas, an injectable product, a degassed injectable product, and combinations thereof.

22. The method of claim 20, wherein prior to displacing said driver, said method further includes:
removing a cap from said dispensing end of said needle-less injector.

23. The method of claim 20, wherein after displacing said adjustment switch toward said dispensing end of said needle-less injector, said method further includes:
removing said adjustment switch from said needle-less injector.

24. A method of administering a needle-less injection with an adjusted volume of an injectable product, comprising:
providing a needle-less injector, comprising
an adjustment switch to adjust said contents of said needle-less injector,
a driver to force a volume of said contents of said needle-less injector out of said needle-less injector through an orifice, and
a transecting member attached to said adjustment switch, to provide mechanical interaction between said adjustment switch and said driver,
wherein displacement of said adjustment switch in the direction of a dispensing end of said needle-less injector causes said driver to move toward said dispensing end of said needle-less injector; and
displacing said driver toward said dispensing end to expel a portion of said injectable product leaving said adjusted volume within said needle-less injector; and
administering an injection with said needle-less injector.

25. The method of claim 24, wherein said injectable product is a degassed injectable product.

26. The method of claim 24, wherein displacing said driver results in an expulsion of air or gas from said needle-less injector in addition to expulsion of said portion of said injectable product.

27. The method of claim 24, wherein prior to displacing said driver, said method further includes:
removing a cap from said dispensing end of said needle-less injector.

28. The method of claim 24, wherein prior to administering an injection with said needle-less injector, said method further includes:
removing said adjustment switch from said needle-less injector.

* * * * *